United States Patent [19]

Sanner et al.

[11] 4,281,137

[45] Jul. 28, 1981

[54] PURIFICATION OF 2-OXAZOLINES

[75] Inventors: James W. Sanner; Peter W. Owen, both of Midland, Mich.

[73] Assignee: The Dow Chemical Company, Midland, Mich.

[21] Appl. No.: 122,946

[22] Filed: Feb. 20, 1980

[51] Int. Cl.³ .......................................... C07D 263/12
[52] U.S. Cl. ..................................... 548/239
[58] Field of Search ......................... 548/239

[56] References Cited

U.S. PATENT DOCUMENTS 3,326,929  6/1967  Seeliger ............................... 548/239

Primary Examiner—Anton H. Sutto
Attorney, Agent, or Firm—Michael L. Glenn

[57] ABSTRACT

Residual amounts of water and color-causing impurities can be removed from a 2-oxazoline compound by introducing from 0.01 to 25 weight percent of a dialkyl hydrogen phosphite or a halosilane compound to the 2-oxazoline and then distilling the oxazoline. For example, 0.5 weight percent of bis(2-ethylhexyl)hydrogen phosphite was introduced into 100 grams of 2-ethyl-2-oxazoline containing 1000 parts per million (ppm) of water and the mixture was then distilled to yield 2-ethyl-2-oxazoline containing less than 10 ppm of water.

11 Claims, No Drawings

PURIFICATION OF 2-OXAZOLINES

BACKGROUND OF THE INVENTION

This is a novel process for reducing the water content of a 2-oxazoline compound. In particular, this process relates to the treatment of the 2-oxazoline with a dialkyl hydrogen phosphite or a halosilane compound followed by separation of the resultant purified 2-oxazoline.

In the preparation of 2-oxazoline compounds, water and other impurities are coproduced which have a deleterious effect upon the properties of the 2-oxazoline. For example, in the polymerization of a 2-oxazoline the presence of even a small amount of water can cause premature chain termination so that the average molecular weight of the resulting polymer is relatively low.

Seeliger et al. teach in *Angew. Chem. International Ed.*, Vol. 5 (1966) on pages 882–883 that 2-oxazolines can be purified adequately for polymerization purposes by fractional distillation. However, we have observed that the purity of a 2-oxazoline obtained by simple fractional distillation is not generally suitable for polymerization or certain other end uses. U.S. Pat. No. 3,326,929 discloses that 2-oxazolines can also be purified by distillation in the presence of acid chlorides or anhydrides.

SUMMARY OF THE INVENTION

According to this invention, a 2-oxazoline represented by the formula

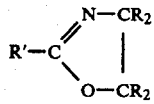

wherein R' is hydrogen, an aryl or aliphatic group having less than 8 carbon atoms and R at each occurrence is independently hydrogen or methyl, said 2-oxazoline, containing residual water and other impurities, is purified in a process comprising the steps of (a) treating the 2-oxazoline with a compound selected from the group consisting of dialkyl phosphites and halosilanes so as to react with substantially all of the water present; and (b) distilling the treated 2-oxazoline to recover the purified oxazoline.

DETAILED DESCRIPTION OF THE INVENTION

2-Oxazoline Compounds

The 2-oxazolines to be purified form a known class of compounds having many members. These oxazoline compounds are conveniently prepared by reacting an alkanolamine with an organic carboxylic acid to form an amide and water followed by cyclodehydration of the amide to an oxazoline. Even though the water of dehydration is continuously removed by distillation during the reaction to promote formation of the 2-oxazoline, the resulting product typically contains residual amounts of water. These residual amounts of water are typically from about 0.01 to about 0.5 percent by weight of the 2-oxazoline product. Many 2-oxazoline compounds are also hygroscopic and will absorb water on standing in contact with moist air. Although the instant process is operable with 2-oxazolines containing as much as about 1 percent water by weight, it is preferable that the 2-oxazoline contain no more than about 0.5 percent water by weight.

The 2-oxazoline compounds prepared in the conventional manner contain impurities which impart color to polymers prepared by homopolymerization or copolymerization of these compounds. We have observed that polymers prepared from 2-oxazoline monomers treated in the manner of this invention are unexpectedly less colored than polymers prepared from monomers which have not been so treated. While the identity of these color-causing impurities is not known, the instant process is very effective in attenuating the undesirable effect of these impurities on the color of an oxazoline polymer.

Of course, R' in the formula for the 2-oxazoline can both represent a variety of moieties, such as, hydrogen, methyl, ethyl, vinyl, isopropenyl, phenyl or tolyl. Preferably, R' is hydrogen, methyl, ethyl or phenyl, most preferably ethyl. Preferably, R at each occurrence is hydrogen.

Phosphite or Chlorosilane Reactants

The dialkyl hydrogen phosphites are well-known compounds. The preferred species are those which hydrolyze readily, produce hydrolysis products which do not codistill with the 2-oxazoline and are commercially available. Especially preferred are dimethyl hydrogen phosphite, dibutyl hydrogen phosphite, diethyl hydrogen phosphite and bis(2-ethylhexyl)hydrogen phosphite, with the latter two of the aforementioned species being most preferred.

The halosilane compounds are silane derivatives bearing at least one halogen substituent and a remaining number of lower alkyl ($C_1$-$C_4$) or hydrogen substituents. The halosilanes are known compounds described in *Kirk-Othmer, Encyclopedia of Chemical Technology*, 2nd Ed., Vol. 18, pp. 181–188 (1969), the relevant portions of which are incorporated herein by reference. Although halogenated derivatives of di-, tri- and higher silanes are operable, the halogenated derivatives of monosilanes are preferred. The halogen substituents can be bromine, chlorine or iodine, but chlorine substituents are preferred. Representative halosilane compounds include trimethylchloromonosilane, methyltrichloromonosilane, dimethyldichloromonosilane, dichloromonosilane, ethyltrichlorosilane, phenyltrichlorosilane, diiodomonosilane and the like. Because of the difficulty in handling the halosilane compounds, the dialkyl hydrogen phosphite compounds are preferred.

Step (a)

The minimum effective quantity of dialkyl hydrogen phosphite or halosilane to be employed in this process depends upon the purity of the 2-oxazoline as well as the phosphite or halosilane employed. Typically, the greater the amount of impurities present, the more phosphite or halosilane will be required to effect purification of the oxazoline. Generally, greater than a stoichiometric amount of the phosphite or halosilane is necessary to efficiently remove the impurities, but a very large excess of the halosilane or phosphite is undesirable because of possible side reactions which will reduce recovery of the 2-oxazoline. Typically, from about 0.1 to about 25 weight percent, preferably about 0.2 to about 10 weight percent, of the phosphite or halosilane is employed based on the 2-oxazoline.

The treatment of the 2-oxazoline compound can be carried out at a temperature of from about 0° C. to about 200° C., preferably about 20° C. to about 150° C.

The pressure during treatment is not critical, with atmospheric pressure being convenient.

The time necessary to effect substantially complete reaction of water and the other impurities is dependent upon a variety of factors, such as the purity of the 2-oxazoline, the identity and quantity of the phosphite or halosilane compound and the temperature during treatment. Typically, at the preferred treatment conditions from about 1 to about 60 minutes are required to effect reaction with substantially all (i.e., about 90 weight percent) of the water present.

Step (b)

The 2-oxazoline can be readily recovered in an essentially pure state by distillation in a manner known to the art. Advantageously, the distillation occurs at reduced pressure at temperatures less than about 130° C., so as to minimize polymerization of the 2-oxazoline.

The following examples are illustrative of the present invention and are not to be construed as limiting the scope thereof. All parts and percentages are by weight unless otherwise specified.

EXAMPLES 1–3

Comparative Experiment

To 100 grams of 2-ethyl-2-oxazoline containing about 1000 parts per million (ppm) of water was charged with stirring 0.5 grams of diethyl hydrogen phosphite, bis(2-ethylhexyl)hydrogen phosphite or dimethyldichlorosilane at a temperature of about 20° C. The reaction mixture was heated to 128° C. at atmospheric pressure to distill 2-ethyl-2-oxazoline. A control run not embodying this invention was also made in which the 2-ethyl-2-oxazoline was similarly distilled without the addition of any purification agent.

A small sample of the 2-ethyl-2-oxazoline distillate was subjected to gas chromatographic analysis in the conventional manner to determine the quantity of water present. A ten-gram portion of each distillate was polymerized by adding 0.1 gram of methyl tosylate and then heating to the boiling point of the mixture for 3 minutes after which the exothermic polymerization reaction proceeded spontaneously to completion. The resulting polymer was dissolved in water to prepare a 5 percent solution and the color of this solution compared to standard solutions in the manner taught in the "Standard Method of Test for Color of Clear Liquids", ASTM Method No. D-1209-69, *Annual Book of ASTM Standards*, Part 27, American Society for Testing and Materials (1974). The purification agent, the water content of the distillate and color of the polymer solution are tabulated in Table I.

TABLE I

| Example | Purification Agent | Water Content (ppm) | Polymer Color |
| --- | --- | --- | --- |
| 1 | $(C_2H_5O)_2P(O)H$ | 10 | 10 |
| 2 | $(C_8H_{17}O)_2P(O)H$ | 10 | 10 |
| 3 | $(CH_3)_2SiCl_2$ | — | 15 |
| Comparative | | | |

TABLE I-continued

| Example | Purification Agent | Water Content (ppm) | Polymer Color |
| --- | --- | --- | --- |
| Experiment* | None | 250 | 30 |

*Not an embodiment of this invention.

What is claimed is:

1. A process for purifying a 2-oxazoline compound represented by the formula

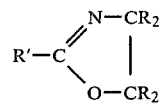

wherein R' is hydrogen, an aryl or aliphatic group having less than 8 carbon atoms and R at each occurrence is independently hydrogen or a methyl group, said 2-oxazoline containing residual water and other impurities, said process comprising the steps of:
  (a) treating the 2-oxazoline with a dialkyl phosphite or a silane bearing at least one halogen substituent and a remaining number of hydrogen, phenyl or $C_1$ to $C_4$ alkyl substituents, so as to react with substantially all of the water present; and
  (b) distilling the treated 2-oxazoline to recover the purified oxazoline.

2. The process as described in claim 1 wherein the 2-oxazoline prior to treatment contains from about 0.01 to about 0.5 percent water by weight of the 2-oxazoline.

3. The process as described in claim 1 wherein R' is hydrogen, methyl, ethyl, vinyl, isopropenyl, phenyl or tolyl.

4. The process as described in claim 1 wherein R' is hydrogen, methyl, ethyl or phenyl.

5. The process as described in claim 4 wherein R is hydrogen.

6. The process as described in claim 5 wherein R' is ethyl.

7. The process as described in claim 3 wherein the 2-oxazoline is treated in Step (a) with a dialkyl phosphite selected from the group consisting of dimethyl hydrogen phosphite, dibutyl hydrogen phosphite, diethyl hydrogen phosphite and bis(2-ethylhexyl)hydrogen phosphite.

8. The process as described in claim 7 wherein the dialkyl phosphite is diethyl hydrogen phosphite or bis(2-ethylhexyl)hydrogen phosphite.

9. The process as described in claim 8 wherein the 2-oxazoline is treated in Step (a) with a halosilane selected from the group consisting of monosilanes bearing at least one chlorine substituent and a remaining number of lower alkyl or hydrogen substituents.

10. The process as described in claim 8 wherein the dialkyl phosphite is present in step (a) in an amount from about 0.1 to about 25 weight percent based on the 2-oxazoline.

11. The process as described in claim 3 wherein the 2-oxazoline is treated in Step (a) with a silane selected from the group consisting of trimethylchloromonosilane, methyltrichloromonosilane, dimethyldichloromonosilane, dichloromonosilane, ethyltrichlorosilane, phenyltrichlorosilane and diiodomonosilane.

* * * * *